(12) United States Patent
Roitman et al.

(10) Patent No.: US 7,226,794 B2
(45) Date of Patent: Jun. 5, 2007

(54) SURFACE-ENHANCED RAMAN SPECTROSCOPY FOR BIOSENSOR SYSTEMS AND METHODS FOR DETERMINING THE PRESENCE OF BIOMOLECULES

(75) Inventors: Daniel B. Roitman, Menlo Park, CA (US); Danielle R. Chamberlin, Belmont, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 10/824,548

(22) Filed: Apr. 14, 2004

(65) Prior Publication Data

US 2005/0233474 A1 Oct. 20, 2005

(51) Int. Cl.
G01N 33/551 (2006.01)
(52) U.S. Cl. ............ 436/525; 436/518; 436/524; 435/7.1; 435/283.1; 435/287.1; 435/287.2; 356/300; 356/301
(58) Field of Classification Search ............ 435/4, 435/6, 7.1, 174, 283.1, 287.2, 288.7; 422/80, 422/82.05, 50, 55, 61, 68.1; 436/501, 518, 436/524, 525, 86, 164; 356/300, 301
See application file for complete search history.

(56) References Cited

U.S. PATENT DOCUMENTS

| 5,567,628 | A | * | 10/1996 | Tarcha et al. ............... 436/525 |
| 6,025,202 | A | * | 2/2000 | Natan ......................... 436/104 |
| 6,149,868 | A | * | 11/2000 | Natan et al. ............. 422/82.05 |
| 6,242,264 | B1 | * | 6/2001 | Natan et al. ................ 436/171 |
| 6,323,989 | B1 | * | 11/2001 | Jacobson et al. ........... 359/296 |
| 6,361,944 | B1 | | 3/2002 | Mirkin et al. |
| 6,579,721 | B1 | * | 6/2003 | Natan et al. ................ 436/164 |
| 6,776,962 | B1 | * | 8/2004 | Boss et al. ............... 422/82.11 |
| 2003/0059820 | A1 | * | 3/2003 | Vo-Dinh ........................ 435/6 |
| 2003/0099940 | A1 | * | 5/2003 | Empedocles et al. .......... 435/6 |
| 2003/0211488 | A1 | * | 11/2003 | Mirkin et al. .................. 435/6 |
| 2003/0231304 | A1 | | 12/2003 | Chan et al. |
| 2004/0023261 | A1 | * | 2/2004 | Bruchez et al. ................ 435/6 |
| 2005/0089901 | A1 | * | 4/2005 | Porter et al. ................... 435/6 |

FOREIGN PATENT DOCUMENTS

WO WO 03/078649 A2 9/2003

OTHER PUBLICATIONS

Cao et al. Nanoparticles with Raman spectroscopic Fingerprints for DNA and RNA Detection, Aug. 2002, Science, vol. 297, pp. 1536-1540.*

Feldheim, Title: "Assembly Of Metal Nanoparticle Arrays Using Molecular Bridges", The Electrochemical Society Interface, 2001, pp. 22-25.

* cited by examiner

Primary Examiner—Long V. Le
Assistant Examiner—Melanie J. Yu

(57) ABSTRACT

Biosensors, methods, and systems for determining the presence of biomolecules using surface-enhanced Raman spectroscopy (SERS) are provided.

9 Claims, 10 Drawing Sheets

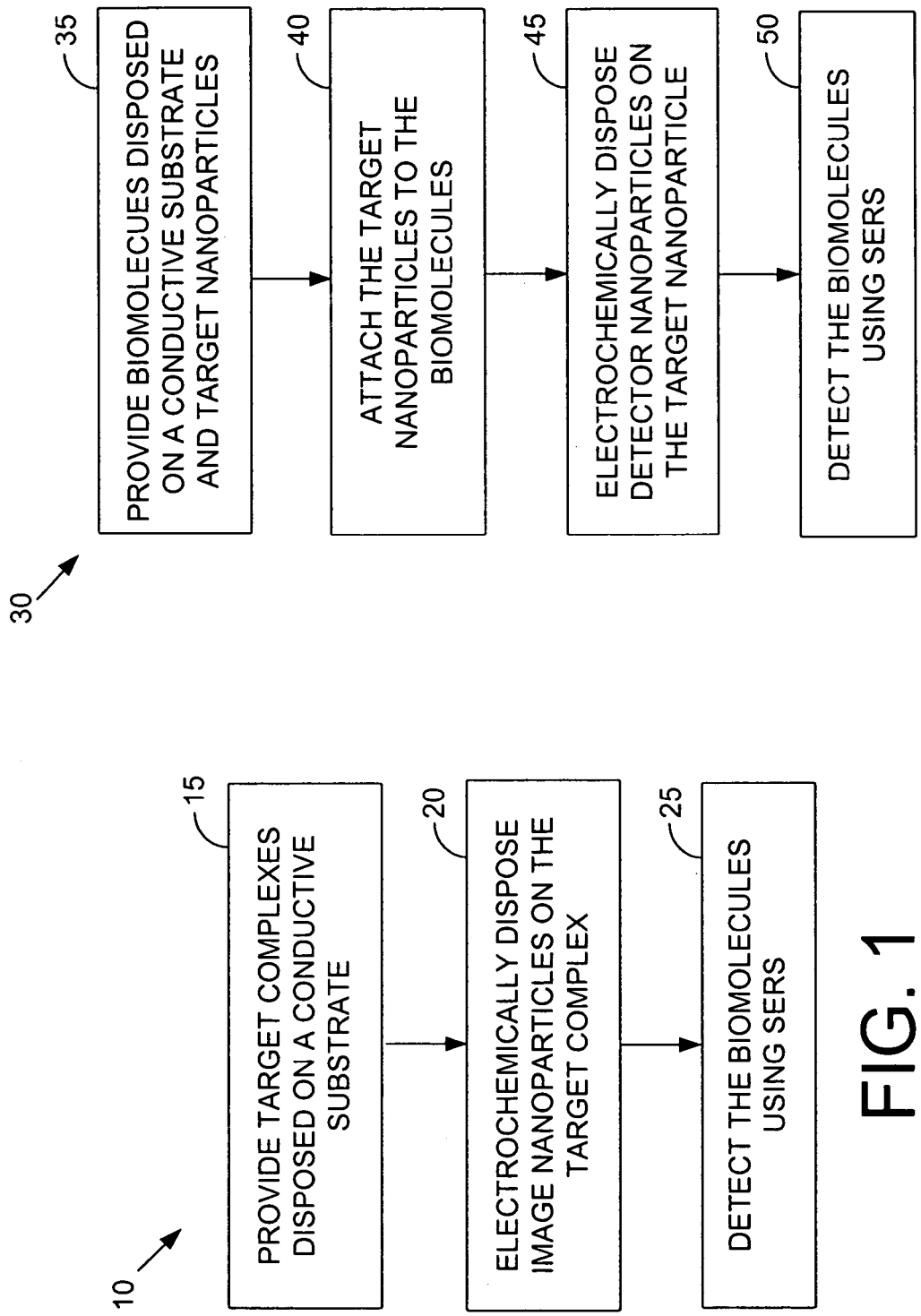

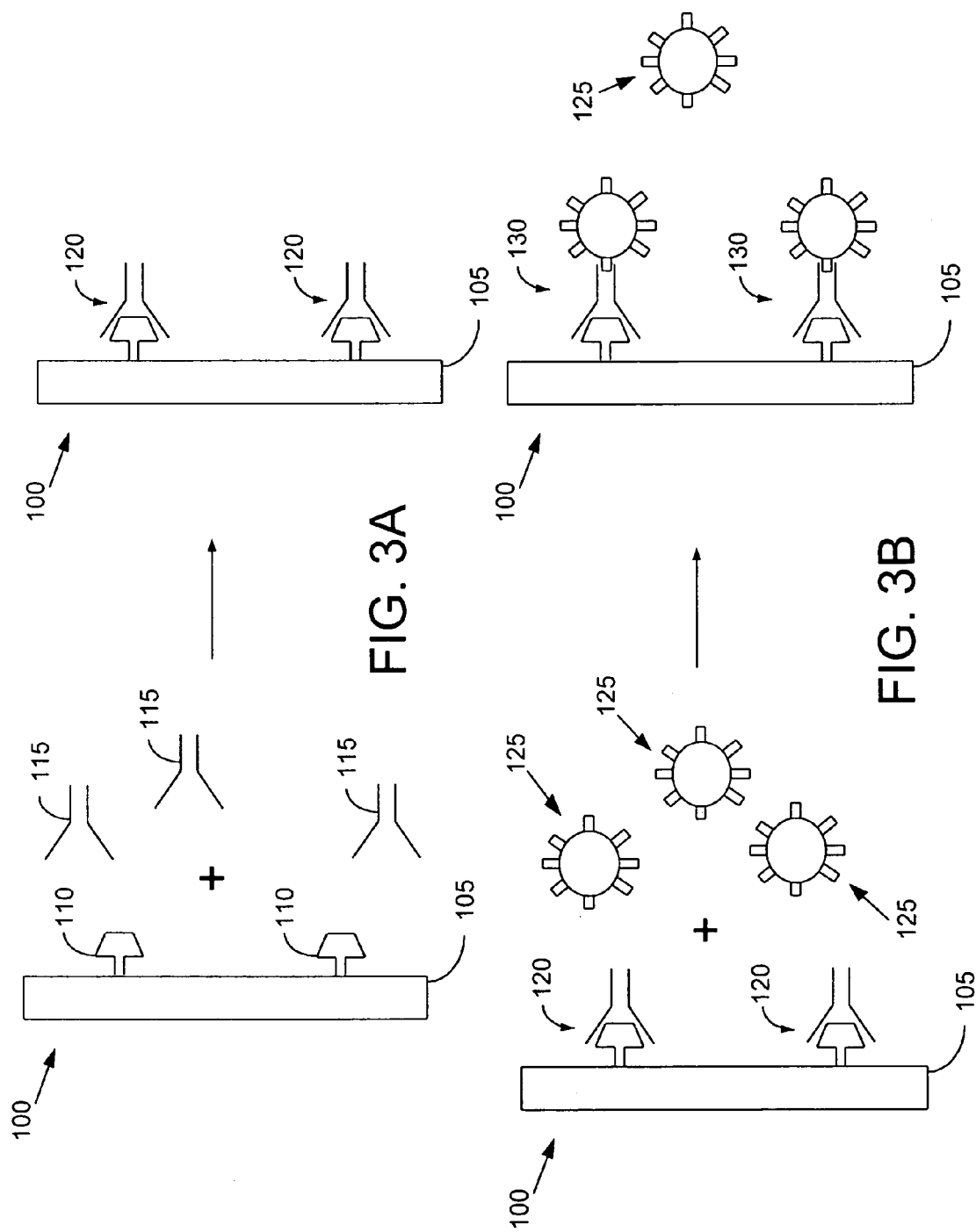

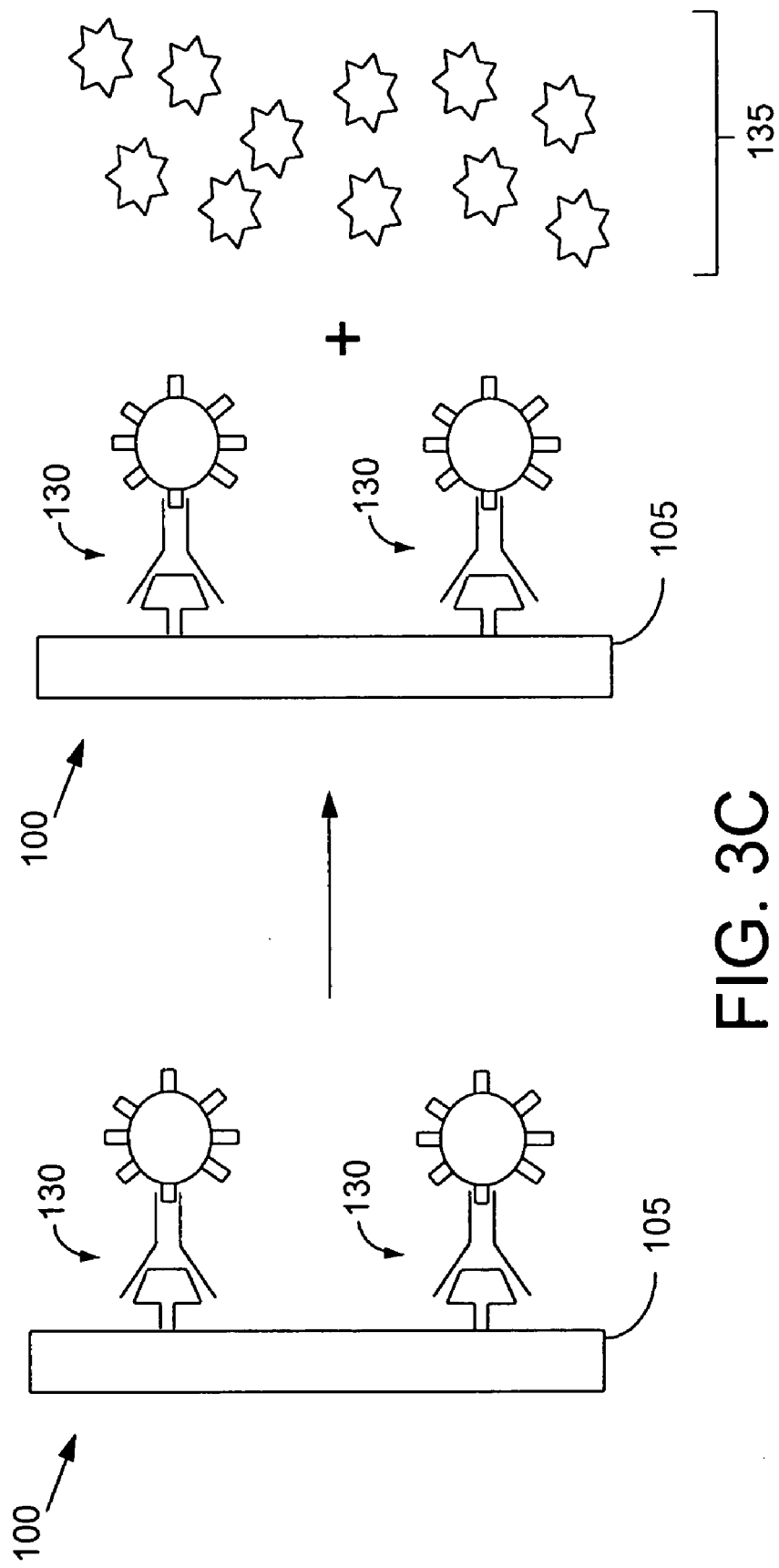

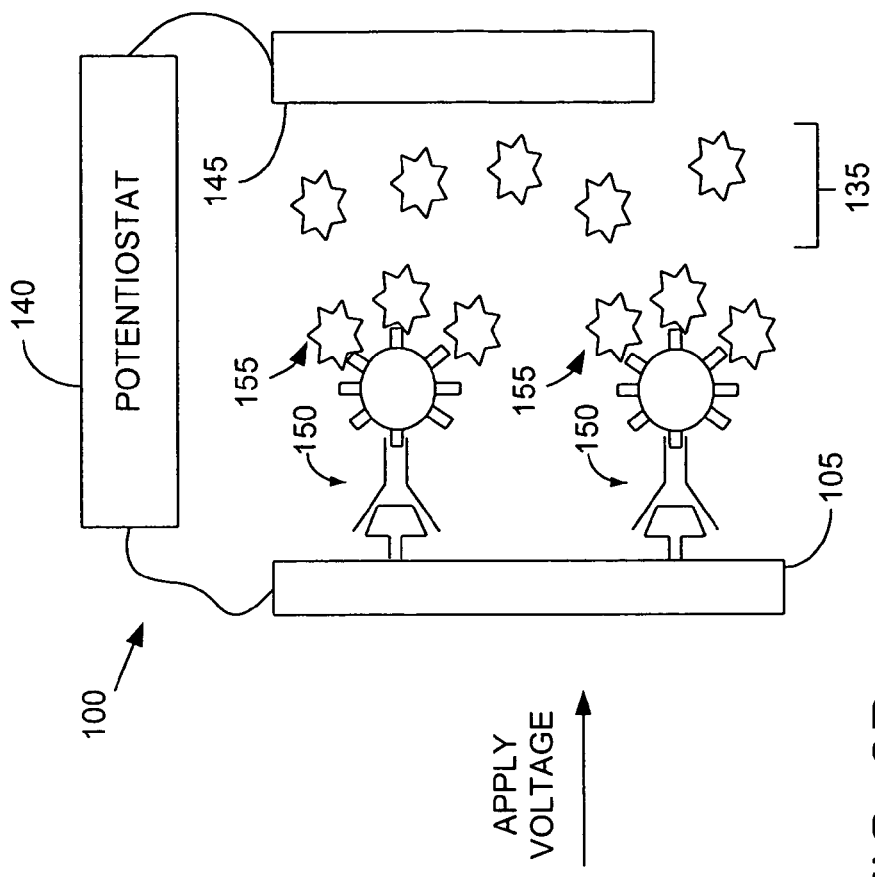
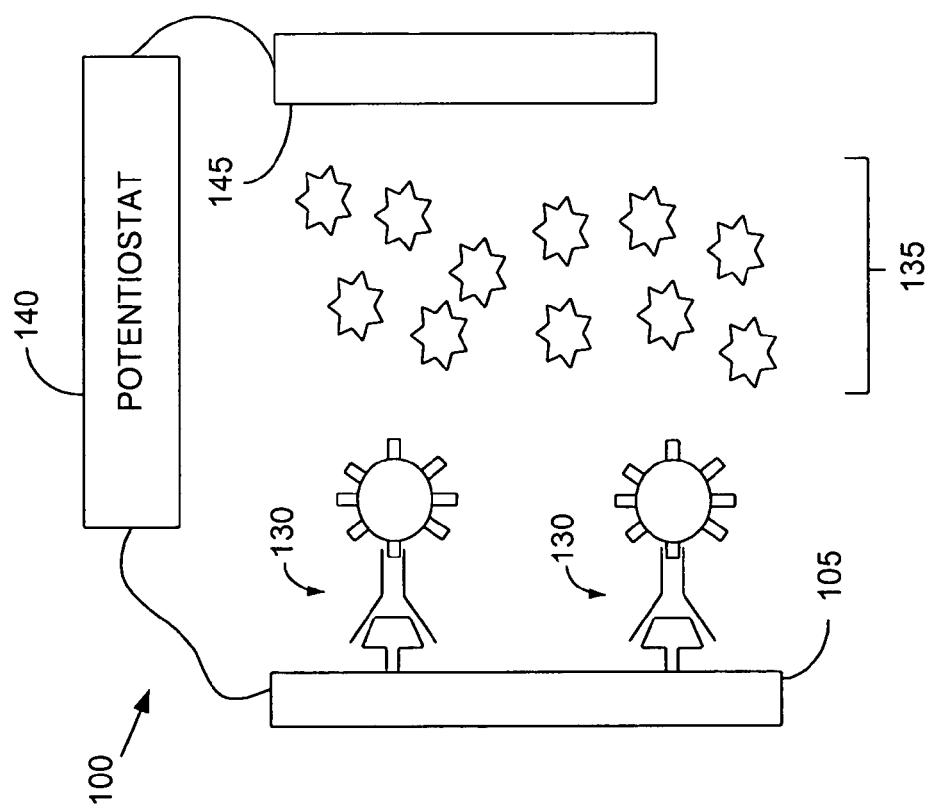
FIG. 3D

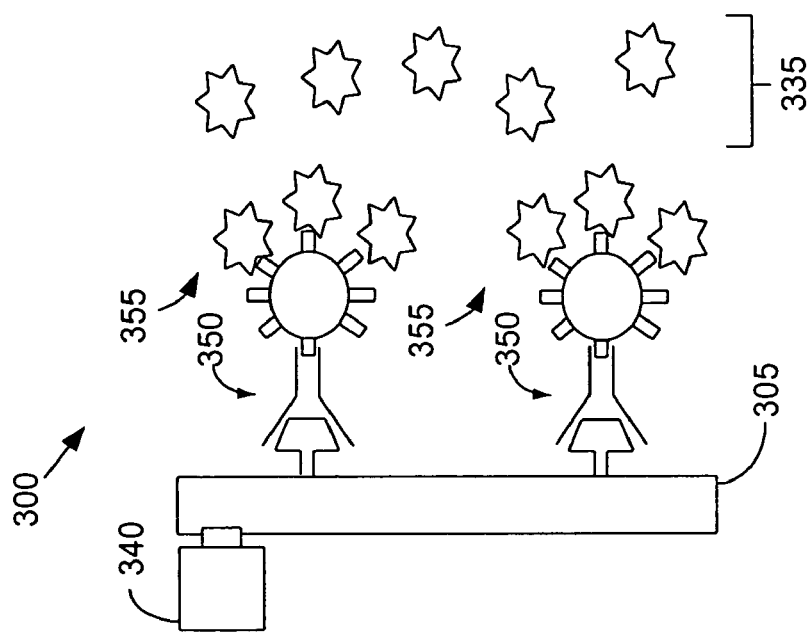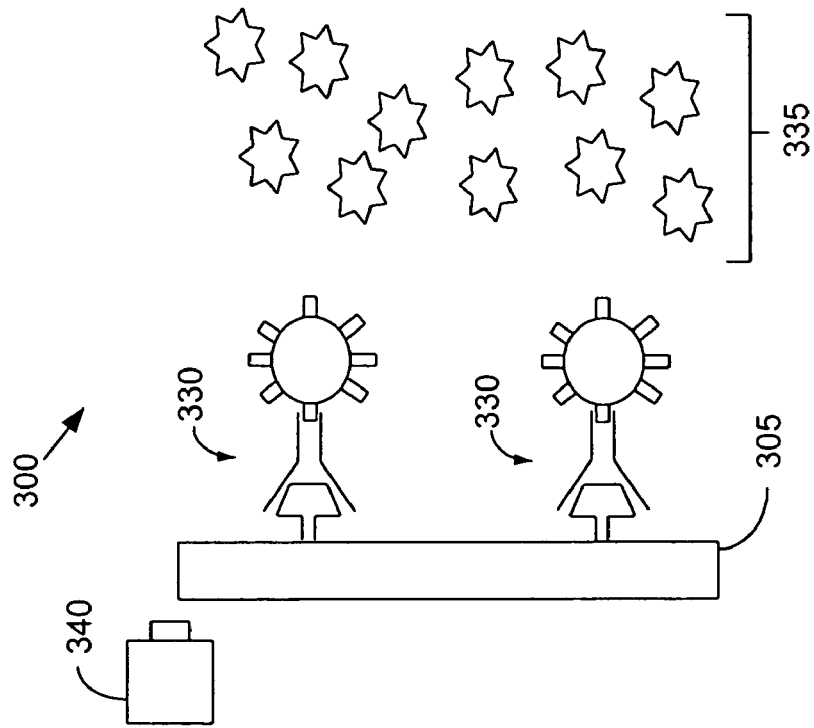
FIG. 5D

SURFACE-ENHANCED RAMAN SPECTROSCOPY FOR BIOSENSOR SYSTEMS AND METHODS FOR DETERMINING THE PRESENCE OF BIOMOLECULES

BACKGROUND

In general, a biosensor is capable of identifying biomolecules such as polynucleotides and polypeptides. One method includes introducing a biomolecule sample containing target biomolecules to a substrate having probes deposited thereon. The probe can include various biomolecules that can interact with target biomolecules, while the substrate can be a solid surface such as silica, surface-derivatized glass, polypropylene, and activated polyacrylamide. The target biomolecules can then interact (e.g., bond or hybridize) with one or more of the probes. Subsequently, the interaction can be analyzed based on the presence and location of the target biomolecule-probe interaction, which can be determined by one or more detection techniques such as optical, radiochemical, and electrochemical techniques.

Another method includes introducing a substrate having target biomolecules disposed thereon to a solution that can include complimentary polynucleotide or polypeptide probe samples derived from biomolecules that have been tagged with fluorescent dyes. The probe material interacts selectively with target biomolecues only where complimentary bonding sites occur. In other words, probe biomolecules with similar chemical characteristics (e.g., nucleotide sequence or amino acid sequence) to the target biomolecule interact with the target molecules, while dissimilar probe biomolecules do not significantly interact with the target biomolecules. Thereafter, the presence and quantity of bound probe biomolecules can be detected and analyzed in a manner similar to the detection techniques discussed above.

In regard to detection of target biomolecules, the ability to detect and identify trace quantities of chemicals has become increasingly important in virtually every scientific discipline, ranging from part per billion analyses of pollutants in sub-surface water to analysis of cancer treatment drugs in blood serum. Surface-enhanced Raman spectroscopy (SERS) has proven to be one of the most sensitive methods for performing such chemical analyses by the detection of a single molecule. (Nie, S. and S. R. Emory, "Probing Single Molecules and Single Nanoparticles by Surface Enhanced Raman Scattering", *Science,* 275,1102 (1997)). A Raman spectrum, similar to an infrared spectrum, includes a wavelength distribution of bands corresponding to molecular vibrations specific to the sample being analyzed (the analyte). In the practice of Raman spectroscopy, the beam from a light source, generally a laser, is focused upon the sample to thereby generate inelastically scattered radiation, which is optically collected and directed into a wavelength-dispersive or Fourier transform spectrometer in which a detector converts the energy of impinging photons to electrical signal intensity.

Historically, the very low conversion of incident radiation to inelastic scattered radiation limited Raman spectroscopy to applications that were difficult to perform by infrared spectroscopy, such as the analysis of aqueous solutions. It was discovered in 1974, however, that when a molecule in close proximity to a roughened silver electrode is subjected to a Raman excitation source, the intensity of the signal generated is increased by as much as six orders of magnitude. (Fleischmann, M., Hendra, P. J., and McQuillan, A. J., "Raman Spectra of Pyridine Adsorbed at a Silver Electrode," *Chem. Phys. Lett,* 26, 123, (1974), and Weaver, M. J., Farquharson, S., Tadayyoni, M. A., "Surface-enhancement factors for Raman scattering at silver electrodes. Role of adsorbate-surface interactions and electrode structure," *J. Chem. Phys.,* 82, 4867–4874 (1985)). Briefly, incident laser photons couple to free conducting electrons within the metal which, confined by the particle surface, collectively cause the electron cloud to resonate. The resulting surface plasmon field provides an efficient pathway for the transfer of energy to the molecular vibrational modes of a molecule within the field, and thus generates Raman photons.

The described phenomenon occurs however only if the following two conditions are satisfied: (1) that the free-electron absorption of the metal can be excited by light of wavelength between 250 and 2500 nanometers (nm), preferably in the form of laser beams; (2) that the metal employed is of the appropriate size (normally 5 to 1000 nm diameter particles, or a surface of equivalent morphology), and has optical properties necessary for generating a surface plasmon field. (Weaver, *J. Chem. Phys.,* 82, 4867–4874 (1985), and Pettinger, *J. Chem. Phys.,* 85, 7442–7451 (1986), supra).

Analyses for numerous chemicals and biochemicals by SERS has been demonstrated, but none of the foregoing techniques is capable of providing quantitative measurements with reproducible results.

SUMMARY

Biosensors, methods, and systems for determining the presence of biomolecules using surface-enhanced Raman spectroscopy (SERS) are provided. Briefly described, one exemplary system, among others, includes a first target complex disposed on a first conductive substrate, a first detector nanoparticle disposed on a first target nanoparticle of the first target complex, and a SERS system capable of detecting a SERS signal specific for the first target biomolecule. The first target complex includes a first target biomolecule and a first target nanoparticle. The first target nanoparticle is disposed on the first target biomolecule. The first detector nanoparticle is electrochemically deposited on the first target nanoparticle.

An exemplary method for determining the presence of biomolecules using the SERS system can be broadly summarized by the following steps: providing a first target biomolecule, a first target nanoparticle, and a first detector nanoparticle; forming a first detector complex electrochemically on a conductive substrate, wherein the first detector complex includes the first target biomolecule, the first target nanoparticle, and the first detector nanoparticle, wherein the first detector nanoparticle is disposed on the first target nanoparticle, wherein the first target nanoparticle is disposed on the first target biomolecule, and wherein the first target biomolecule is disposed on the conductive substrate; directing a laser at the first detector complex, wherein the interaction of the laser with the first detector complex produces a SERS signal specific for the first target biomolecule; and detecting the SERS signal.

Other systems, methods, features and/or advantages of the present disclosure will be, or become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

Aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1 is a flow diagram illustrating a representative embodiment of a process for determining the presence of a biomolecule.

FIG. 2 is a flow diagram illustrating a representative embodiment of a process for determining the presence of a biomolecule.

FIGS. 3A through 3E are schematic diagrams of a process for determining the presence of a biomolecule.

FIGS. 5A through 5E are schematic diagrams of another process for determining the presence of a biomolecule.

DETAILED DESCRIPTION

Figure 3E:
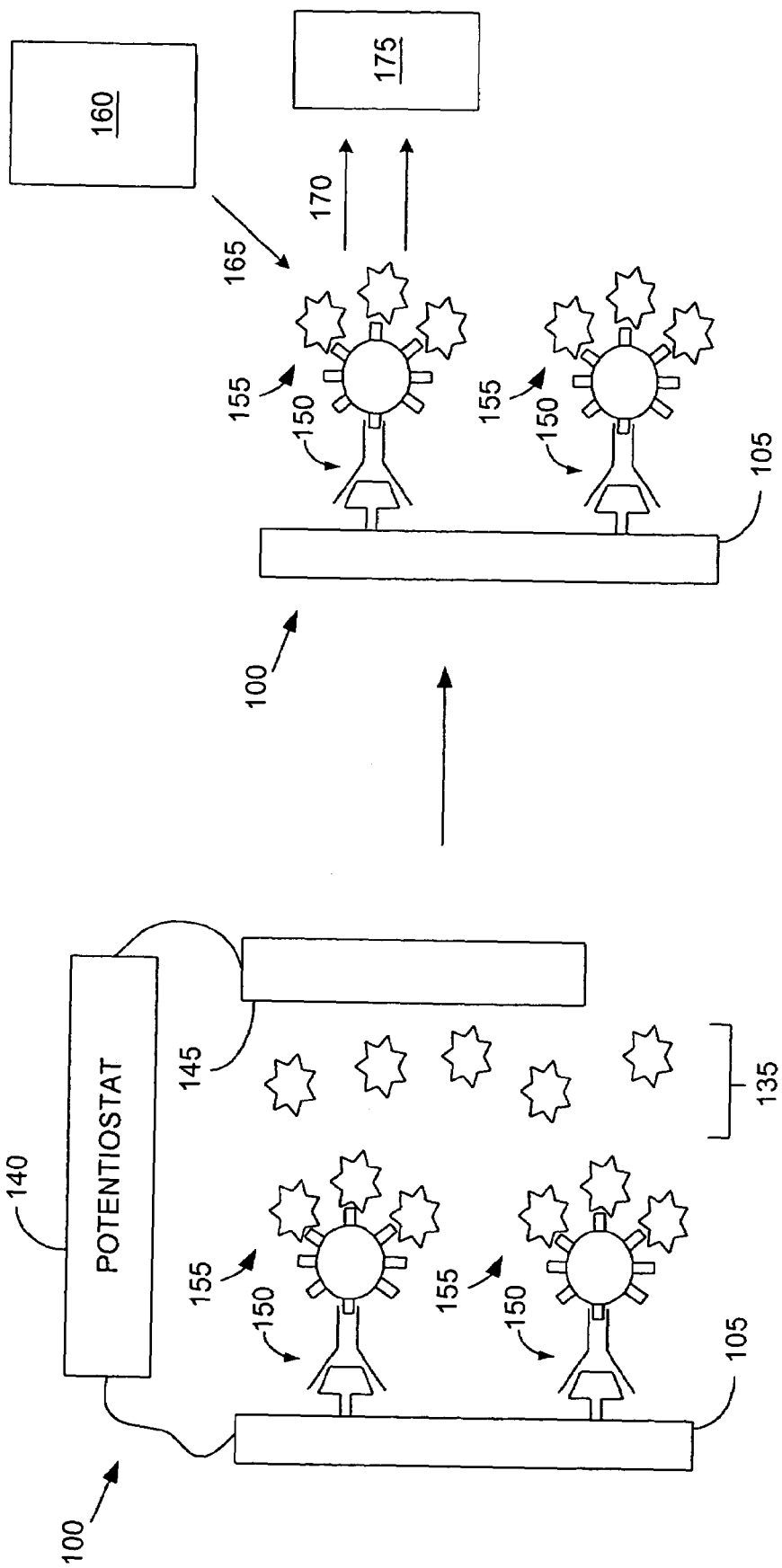

As will be described in detail here, biosensors, methods, and systems capable of determining the presence of biomolecules such as, for example, deoxyribonucleic acid (DNA), ribonucleic acid (RNA), nucleotides, oligonucleotides, nucleosides, proteins, peptides, polypeptides, and antibodies, are provided. In particular, surface-enhanced Raman spectroscopy (SERS) can be used to determine the presence, qualitatively and/or quantitatively, of one or more types of biomolecules.

In general, determining the presence of a target biomolecule (i.e., the biomolecule of interest) is accomplished using SERS. First, detector nanoparticles (e.g., silver metal nanoparticles) can be associated with the target biomolecule. In this regard, a target nanoparticle (e.g., a gold metal nanoparticle) is deposited selectively on the target biomolecule through specific interactions between the target biomolecule and the target nanoparticle. The target biomolecule and the target nanoparticle can selectively interact through biological interactions and/or chemical interactions. Then detector nanoparticles are electrochemically deposited from a solution of detector nanoparticles on the target nanoparticle.

Subsequently, a laser (e.g., laser beam energy) is directed at the detector nanoparticles disposed on the target biomolecule and the incident laser photons couple to free conducting electrons within the detector nanoparticles which, confined by the detector nanoparticles surface, collectively cause the electron cloud to resonate. The resulting surface plasmon field provides an efficient pathway for the transfer of energy to the molecular vibrational modes of the target biomolecule within the field, and thus generates Raman photons (a detectable SERS signal) specific for the target biomolecule.

Since the interaction between the target nanoparticle and the target biomolecule is selectively controlled, a direct correlation can be made between the detected detector nanoparticles deposited on the target nanoparticle and the target biomolecule. Therefore, the target biomolecule can be qualitatively identified and/or quantitatively measured using SERS.

In some cases the Raman cross-section of the target biomolecule is not large enough to provide adequate sensitivity for the application. In these cases a marker molecule with a large Raman cross-section (strong Raman signature) can be attached to the target biomolecule before the detector nanoparticles are attached to the target nanoparticles. (Cao et al., *Science* 297 p. 1536 (2002)). Alternatively, the marker molecule can be attached to the target nanoparticle. The marker molecule can include, but is not limited to, members of the rhodamine family, the cytochrome family, and the pyridine family. In particular, the marker molecule can include, but is not limited to, Rhodamine 6G, Cy3, Cy5, and pyridine.

The biological interactions can include, but are not limited to, bonding or hybridization among one or more biological functional groups located on the target biomolecule and the target nanoparticle. In this regard, the target nanoparticles can include one or more biological functional groups that selectively interact with one or more biological functional groups of the target biomolecule. The chemical interaction can include, but is not limited to, bonding among one or more functional groups (e.g., organic and/or inorganic functional groups) located on the target biomolecule and the target nanoparticle. Thus, the target nanoparticle and the target biomolecule can selectively interact with one another to form a "target complex."

As indicated above, the detector nanoparticles are electrochemically deposited on the target nanoparticle of the target complex. The electrochemical reaction can be facilitated by the target biomolecule being deposited on a conductive substrate. The target biomolecule can be deposited onto the conductive substrate before or after the formation of the target complex. The target biomolecule attaches to the conductive substrate through one or more selective biological interactions with one or more biological probes disposed on the conductive substrate.

The electrochemical deposition of the detector nanoparticles on the target nanoparticle of the target complex occurs when a solution of detector nanoparticles is introduced to the target complex. Subsequently, an electric potential is applied to the conductive substrate. The potential can be generated by, for example, the following: instruments such as potentiostats or galvanostats, a battery system capable of supplying appropriate voltages, or contacting a foreign conductor having a different work function than the conductive substrate. These methods can catalyze the deposition of the detector nanoparticles on the target complex. In particular, the target nanoparticle acts as a nucleation site to catalytically deposit the detector nanoparticles on the target complex to form the detector complex.

The electrochemical deposition of the detector nanoparticles can be precisely controlled by methods described above. In particular, the morphology and thickness of the detector nanoparticles can be precisely controlled and reproducibly practiced, which, as mentioned above, enables the use of SERS to qualitatively identify and/or quantitatively measure the presence of the target biomolecule.

FIG. 1 is a flow diagram illustrating an exemplary process 10 for determining the presence of a target biomolecule. In block 15, target complexes are disposed on a conductive substrate. The target complexes can include, but are not limited to, target biomolecules, target nanoparticles, biomolecule probes, and combinations thereof. Additional details regarding the conductive substrate, the target biomolecule, the target nanoparticle, and the biomolecule probe is discussed below. In block 20, the detector nanoparticles are electrochemically deposited on the target complex. In block 25, the target biomolecules can be detected using a SERS detection system by directing a laser beam on the detector nanoparticle and detecting the generated Raman photons specific for the target biomolecule.

The biomolecule probe can include probes that are capable of attaching to the conductive substrate. In addition, the biomolecule probe is capable of selectively attaching to specific target biomolecules. For example, the biomolecule probes can include, but are not limited to, deoxyribonucleic acid (DNA), ribonucleic acid (RNA), nucleotides, oligonucleotides, nucleosides, proteins, peptides, polypeptides, antigens, antibodies, and combinations thereof.

The target biomolecules can include biomolecules such as, but not limited to, deoxyribonucleic acid (DNA), ribonucleic acid (RNA), nucleotides, oligonucleotides, nucleosides, proteins, peptides, polypeptides, antigens, antibodies, and combinations thereof.

The conductive substrate can be a conductive substrate that has an affinity for the biomolecule probes and/or can be coated with a material having an affinity for the biomolecule probes. For example, the conductive substrate may be formed of, for example, indium tin oxide (ITO). In addition, the conductive substrate can be designed to have an affinity for different types of biomolecule probes so that multiple biomolecules can be tested at one time. Furthermore, the surface of the conductive substrate can be designed to interact with specific biomolecule probes at predetermined positions (patterned) on the conductive substrate. Thus, biosensors can be designed to test for the presence of one or more target biomolecules.

The target nanoparticles can include nanoparticles made of materials such as, but not limited to, semiconductive materials (e.g., silicon) and metals such as gold, silver, nickel, copper, and platinum. In addition, the target nanoparticles can have one or more moieties and/or one or more functional groups disposed on the target nanoparticle that have an affinity for a particular target biomolecule. Therefore, biosensors can be designed to determine the presence of one or more target biomolecules by exposing the target biomolecules to one or more target nanoparticles having known affinities for the particular target biomolecules.

The target nanoparticles are attached (e.g., biologically and/or chemically) to the target biomolecules, which can be attached to the conductive substrate. Alternatively in another embodiment, the target nanoparticles are attached to the target biomolecules, which are attached (e.g., biologically and/or chemically) to the biomolecule probes. In an additional embodiment, the biomolecule probes are attached to the conductive substrate. In another embodiment, the target nanoparticles are attached to the substrate or are part of the substrate, and the target biomolecules are attached to the target nanoparticles. In another embodiment, the conductive substrate can be on the tip of an optical fiber. In another embodiment, the conductive substrate can be part of a microfluidic chip.

The detector nanoparticle can include, but is not limited to, metal nanoparticles and metal nanoparticle precursors. In particular, the detector nanoparticle can include, for example, a silver nanoparticle, a nickel nanoparticle, a copper nanoparticle, a silver nanoparticle precursor, a nickel nanoparticle precursor, and a copper nanoparticle precursor.

The SERS detection system includes a laser that is directed onto the substrate and a spectrometer that measures the scattered laser light (e.g., T. Vo-Dinh, U.S. patent application 2003/0059820). The laser can be any wavelength, typically it would be of a wavelength between the ultraviolet and the infrared. Typical laser powers are from microwatts up to 10's or 100's of mW. The spectrometer is typically a dispersive spectrometer, in the case of a visible or UV laser, and a Fourier transform spectrometer in the case of an infrared laser. In one embodiment, a holographic notch filter tuned to the laser wavelength is employed to transmit the inelastically scattered photons (the Raman spectrum) and reflect the elastically scattered laser light. In another embodiment, the laser is directed through a confocal microscope. The laser may be directed to the sample through free space or alternatively through an optical fiber. (e.g., T. Vo-Dinh, U.S. Pat. No. 5,864,397).

Having described biosensors, systems, and methods for determining the presence of target biomolecules using SERS, in general, two exemplary embodiments are described below.

EXAMPLE 1

FIG. 2 is a flow diagram illustrating an exemplary process 30 for determining the presence of target biomolecules using SERS. In block 35, target biomolecules and target nanoparticles are provided. The target biomolecules are attached directly or indirectly to a conductive substrate via biological and/or chemical interactions. In block 40, the target nanoparticles are attached, biologically and/or chemically, to the target biomolecules. In block 45, the detector nanoparticles are electrochemically deposited on the target nanoparticles. In block 50, the target biomolecules can be detected using SERS by directing a laser beam on the detector nanoparticle and detecting the generated Raman photons specific for the target biomolecule.

FIGS. 3A through 3E are schematic diagrams collectively illustrating an exemplary process for detecting the presence of a target biomolecule for a biosensor system 100 using SERS. FIG. 3A illustrates the biosensor system 100, where biomolecule probes 110 are disposed on a conductive substrate 105 via biological and/or chemical interactions. In addition, FIG. 3A illustrates introducing target biomolecules 115 to the biomolecule probes 110 to form biomolecule complexes 120.

In this embodiment, the biomolecule probes 110 are attached to the conductive substrate 105 prior to being introduced to the target biomolecule 115. In another embodiment, the biomolecule probes 110 can be attached to the target biomolecule 115 prior to being attached to the conductive substrate 105. In still another embodiment, the biomolecule probes 110 are attached to the conductive substrate 105 prior to being introduced to a target biomolecule/target nanoparticle complex 120.

FIG. 3B is a schematic diagram illustrating the introduction of target nanoparticles 125 to the biomolecule complexes 120 to form target complexes 130. As discussed above, target nanoparticles 125 can be disposed on the target biomolecules 115 by interacting selectively (e.g., via biological and/or chemical interactions) with the target biomolecules 115. In addition, the target nanoparticles 125 can have one or more moieties and/or one or more functional groups disposed on the target nanoparticle 125 that have an affinity for a particular target biomolecule 115.

FIG. 3C is a schematic diagram illustrating the introduction of a solution containing detector nanoparticles 135 to the target complexes 130. FIG. 3D is a schematic diagram illustrating the application of a voltage to the conductive substrate 105 in the presence of the solution of detector nanoparticles 135.

The voltage (cathodic) can be applied by a potentiostat 140 having a counter electrode 145 and a reference electrode (not shown), such as silver/silver chloride (Ag/AgCl). The voltage applied to the conductive substrate initiates the deposition of the detector nanoparticles 135 on the target complexes 130, thereby forming detector complexes 150 on the conductive substrate 105. (General reference, Bard, et al., *Electrochemical Methods: Fundamentals and Application*, $2^{nd}$ Ed. 2000.)

The target nanoparticles 125 act as nucleation points for the formation of detector nanoparticles by electrochemical reduction on the conductive substrate 105. As a result, the detector nanoparticles 135 selectively deposit where the target nanoparticles 125 are disposed on the conductive substrate 105 via the biomolecule probes 110 and target biomolecules 115.

The potentiostat 140 can control the deposition by adjusting the applied voltage to the conductive substrate 105. In general, the applied voltage can range between about minus 1500 millivolts and 1500 millivolts (versus Ag/AgCl reference electrode). However, it should be noted that the applied voltage can vary depending on material for the conductive substrate 105, the target nanoparticle 125, and the detector nanoparticle 135.

FIG. 3E is a schematic diagram illustrating detection of the target biomolecule by directing a laser beam 165 from a laser system 160 at the detector nanoparticle 155 deposited on the target nanoparticle 125. The incident laser photons couple to free conducting electrons within the detector nanoparticles 155, which collectively cause the electron cloud to resonate. The resulting surface plasmon field provides an efficient pathway for the transfer of energy to the molecular vibrational modes of the target biomolecule within the field, and thus generates Raman photons 170 specific for the target biomolecule. Subsequently, the Raman photons are detected using SERS system 175.

The conditions under which the electrochemical deposition of the detector nanoparticles is performed can vary depending upon the design of the biosensor 100. In particular, the following variables can be altered: the type and concentration of the detector nanoparticles 135, the settings of the potentiostat 140, the pH of the solution, the concentration of acid and/or base to achieve the appropriate pH, the temperature of the solution, the type and concentration of the target nanoparticle 115, the type of conductive substrate 105, the type and concentration of the target biomolecule 125, the morphology of the detector nanoparticles 155, and the thickness of the detector nanoparticles 155.

EXAMPLE 2

Figure 4:
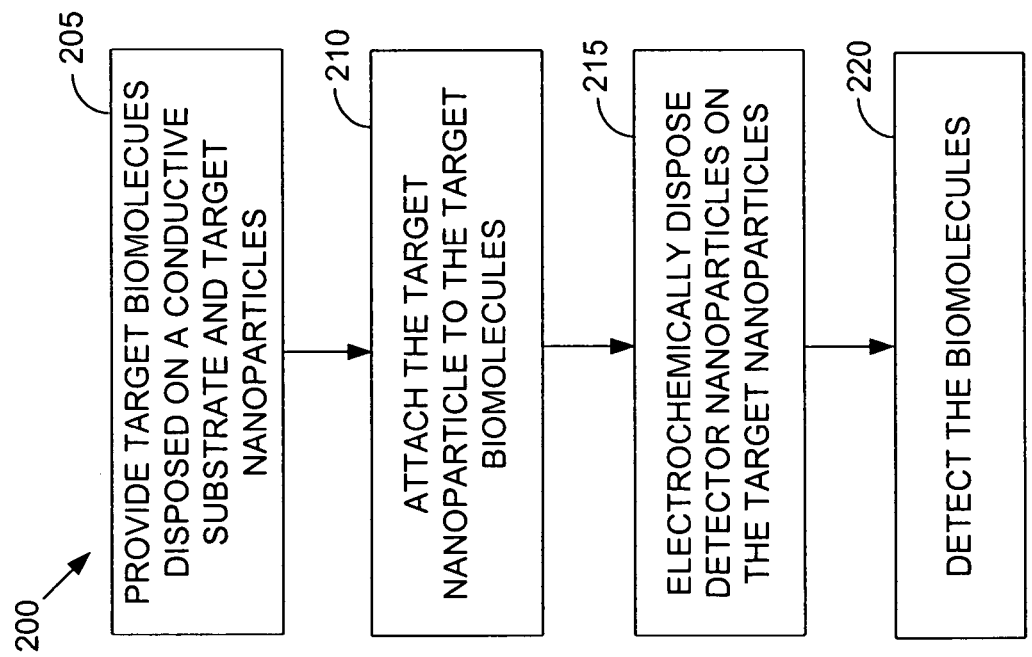
FIG. 4 is a flow diagram illustrating a representative embodiment of a process for determining the presence of a biomolecule.

FIG. 4 is a flow diagram illustrating another exemplary process 200 for determining the presence of target biomolecules using SERS. In block 205, target biomolecules and target nanoparticles are provided. The target biomolecules are attached to a conductive substrate via biological and/or chemical interactions. In block 210, the target nanoparticles are biologically and/or chemically attached to the target biomolecules. In block 215, the detector nanoparticles are electrochemically deposited on the target nanoparticles by contacting a foreign conductive structure to the conductive substrate, which catalyzes (e.g., using galvanostatic forces) the deposition of the detector nanoparticles on the target nanoparticles. In block 220, the target biomolecules can be detected using SERS by directing a laser beam onto the detector nanoparticle and detecting the generated Raman photons specific for the target biomolecule.

Figure 5A:
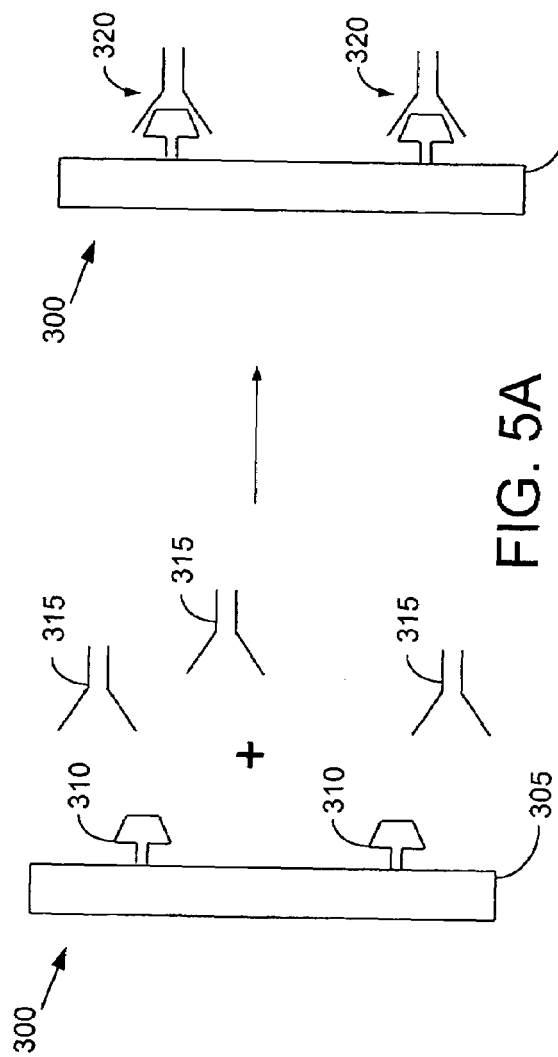

FIGS. 5A through 5E are exemplary schematic diagrams collectively illustrating another process for determining the presence of a target biomolecule for a biosensor system 300 using SERS. FIG. 5A illustrates the biosensor system 300, where biomolecule probes 310 are deposited on a conductive substrate 305. In addition, FIG. 5A illustrates the introduction of target biomolecules 315 to the biomolecule probes 310 to form biomolecule complexes 320.

The biomolecule probes 310, the conductive substrate 305, and the target biomolecules 315 are similar to the biomolecule probe, the conductive substrate, and the target biomolecule, discussed above.

Figure 5B:
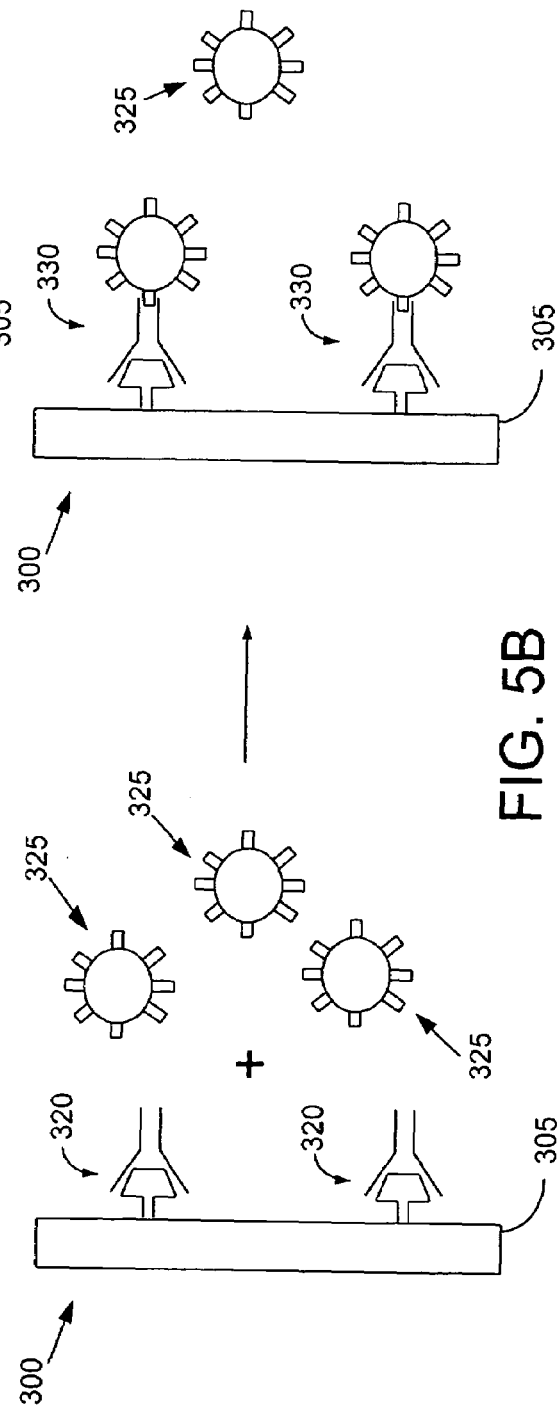

FIG. 5B is a schematic diagram illustrating the introduction of the target nanoparticles 325 to the biomolecule complexes 320 to form target complexes 330. The target nanoparticles 325 are similar to the target nanoparticles described above.

Figure 5C:
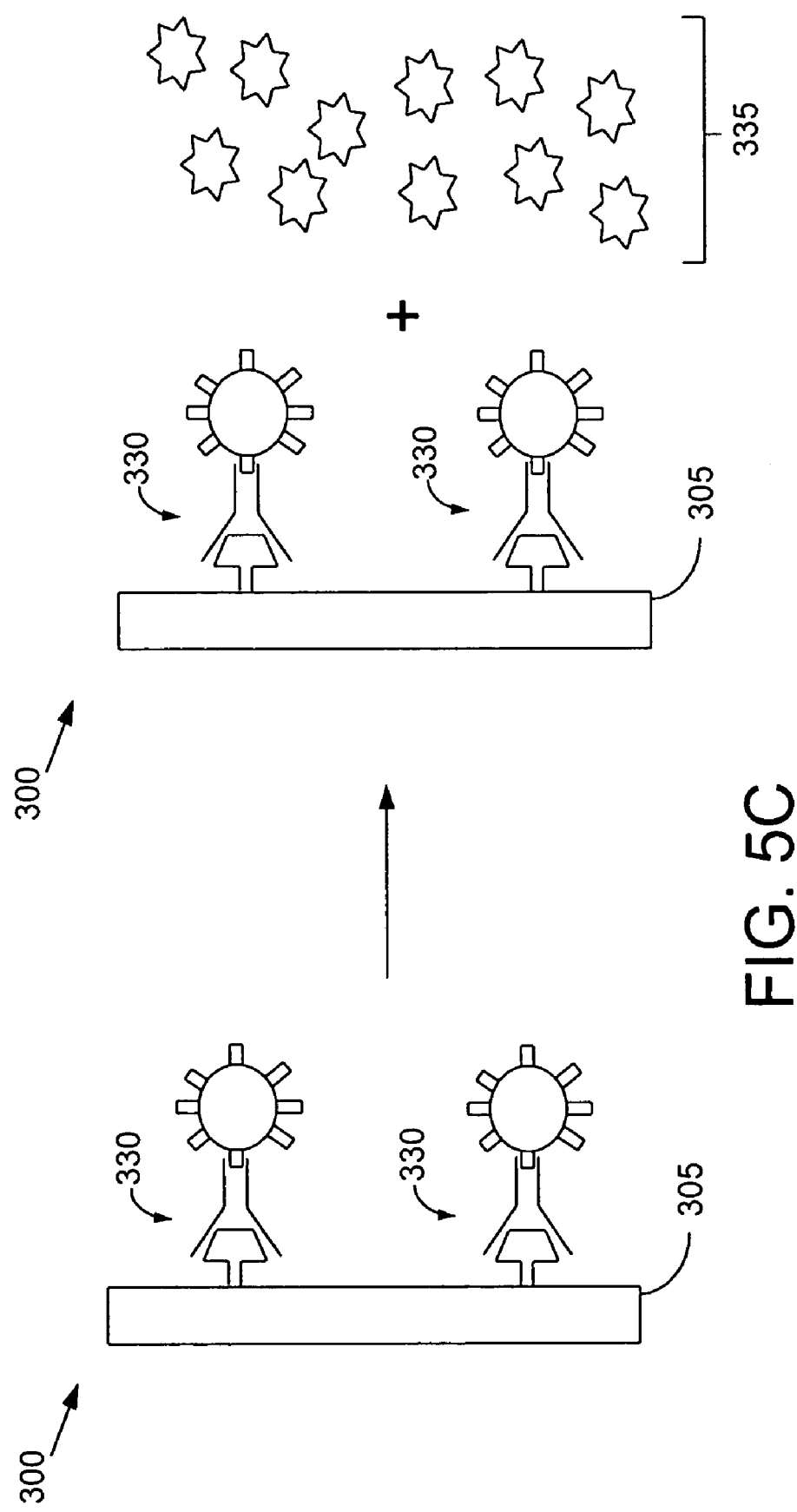

FIG. 5C is a schematic diagram illustrating the introduction of a solution containing detector nanoparticles 335 to the target complexes 330. The detector nanoparticles 335 are similar to the detector nanoparticles described above.

FIG. 5D is a schematic diagram illustrating the introduction of a foreign conductive structure 340 to the conductive substrate 305 in the presence of the solution of detector nanoparticles 335. Contacting a portion of the foreign conductive structure 340 initiates the deposition of the detector nanoparticles 335 on the target complexes 330, thereby forming detector complexes 350 on the conductive substrate 305 having detector nanoparticles 355.

The material for the foreign conductive structure 340 is chosen so that it has a higher tendency to be ionized than the conductive substrate 305. When the foreign conductive structure 340 is contacted to the conductive substrate 305, and both 305 and 340 are immersed in a solution of detector nanoparticles 335, a galvanostatic force is created that results in reduction of the surface of the conductive substrate 305, as well as oxidation of the conductive structure 340. The detector nanoparticles 335 are reduced on the conductive substrate 305. In addition, the target nanoparticles 325 are made of materials that have a higher work function than the conductive substrate 305. The target nanoparticle 325 are similar to the detector nanoparticles described above.

When the electron is transferred to the conductive substrate 305 that has the target nanoparticle 325, the extra electron is concentrated to the surface of the target nanoparticle 325, because the target nanoparticle 325 has a lower energy state than the conductive substrate 305. Therefore, the negative charge is concentrated to the surface of the target nanoparticle 325, which causes localized reduction of the detector nanoparticles 335.

When the foreign conductive structure 340 and the conductive substrate 305 are immersed in the solution having the detector nanoparticles 335 and are electrically connected, the detector nanoparticles 335 are catalytically reduced on the target nanoparticles 325. The target nanoparticles 325 act as nucleation sites for the deposition of the detector nanoparticles 335, and as a result, the detector nanoparticles 335 selectively form at the location where the target nanoparticles 325 are disposed.

The foreign conductive structure 340 can be made of materials such as, but not limited to, copper, nickel, and iron, their alloys, and combinations thereof. Preferably, the foreign conductive structure 340 is a copper conductive structure.

Figure 5E:
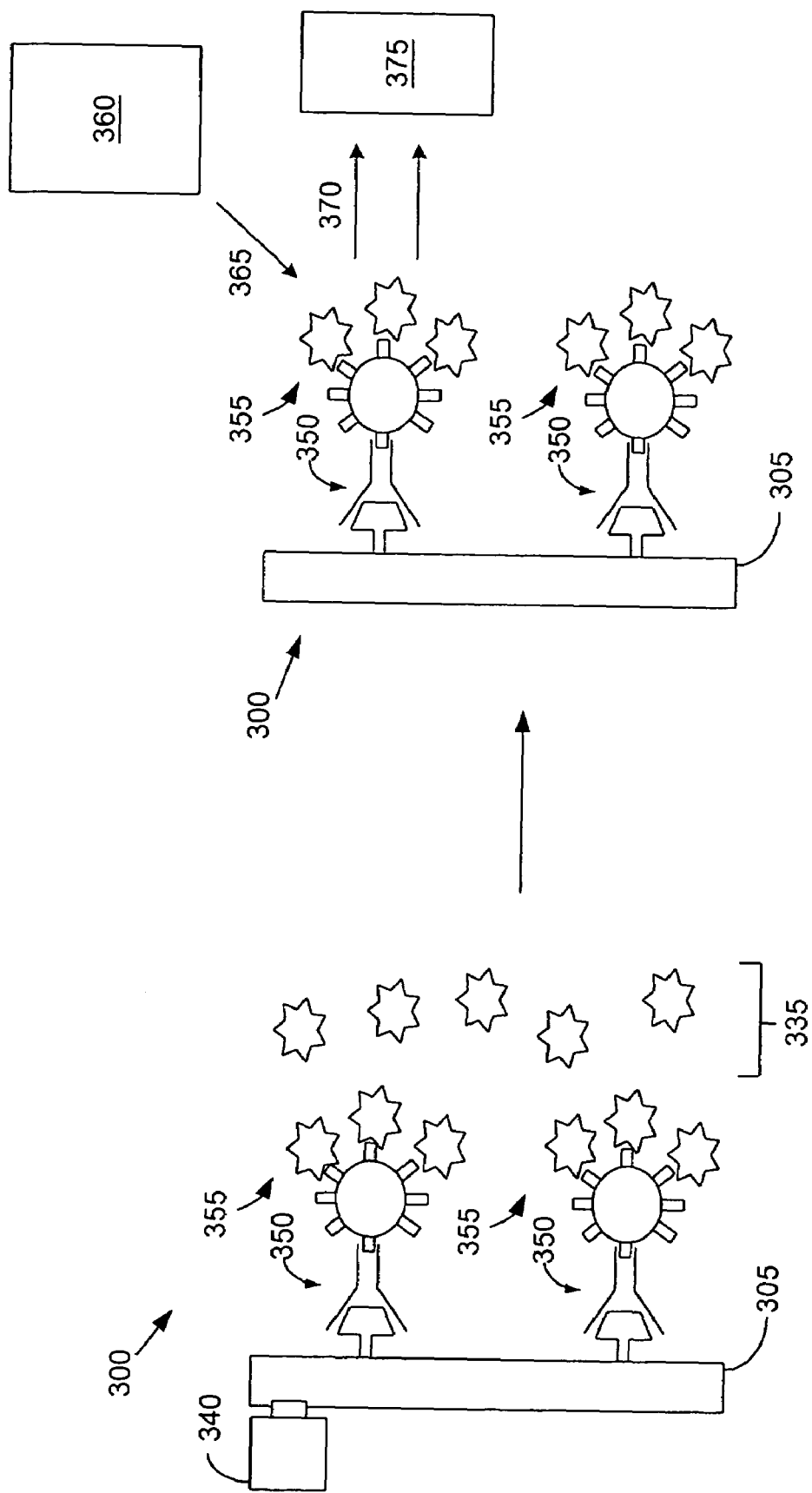

FIG. 5E is a schematic diagram illustrating the removal of the foreign conductive structure 340 from the conductive substrate 305, as well as the detection of the target biomolecule by directing a laser beam 365 from a laser system 360 at the detector nanoparticle 355. The incident laser photons couple to free conducting electrons within the detector nanoparticles which collectively cause the electron cloud to resonate. The resulting surface plasmon field provides an efficient pathway for the transfer of energy to the molecular vibrational modes of the target biomolecule within the field, and thus generates Raman photons 370 specific for the target biomolecule. Subsequently, the Raman photons are detected using SERS detection system 375.

The conditions under which the electrochemical deposition of the detector nanoparticles is performed can vary depending upon the design of the biosensor 300. In particular, the following variables can be altered: the type and concentration of the detector nanoparticles 335, the type of foreign conductive structure 340, the pH of the solution, the concentration of acid and/or base to achieve the appropriate pH, the temperature of the solution, the type and concentration of the target nanoparticle 325, the conductive substrate 305, the type and concentration of the target biomolecule 315, the morphology of the detector nanoparticles 355, and the thickness of the detector nanoparticles 355.

It should be emphasized that the above-described embodiments are merely possible examples of implementations. Many variations and modifications may be made to the above-described embodiments. All such modifications and variations are intended to be included herein within the scope of this disclosure and protected by the following claims.

The following is claimed:

1. A method for determining the presence of biomolecules using a surface-enhanced Raman spectroscopy (SERS) system, comprising:
   providing a first target biomolecule, a first target nanoparticle, and a first detector nanoparticle;
   forming a first detector complex electrochemically on a conductive substrate, wherein the first detector complex includes the first target biomolecule, the first target nanoparticle, and the first detector nanoparticle, wherein the first detector nanoparticle is disposed on the first target nanoparticle, wherein the first target nanoparticle is disposed on the first target biomolecule, and wherein the first target biomolecule is disposed on the conductive substrate;
   directing a laser at the first detector complex, wherein the interaction of the laser with the first detector complex produces a SERS signal specific for the first target biomolecule; and
   detecting the SERS signal, wherein the presence of the SERS signal indicates the presence of the biomolecule.

2. The method of claim 1, wherein forming the first detector complex electrochemically, further comprises:
   forming a first target complex that includes the first target biomolecule and the first target nanoparticle; and
   disposing the first target complex onto the first conductive substrate.

3. The method of claim 1, wherein forming the first detector complex electrochemically, further comprises:
   disposing the first target biomolecule onto the first conductive substrate;
   contacting the first target nanoparticle with the first target biomolecule; and
   forming a first target complex on the first conductive substrate, wherein the first target complex includes the first target biomolecule and the first target nanoparticle.

4. The method of claim 1, wherein the first target nanoparticle includes a gold nanoparticle.

5. The method of claim 1, wherein the first detector nanoparticle includes a silver nanoparticle.

6. The method of claim 1, wherein forming a first detector complex, comprises:
   applying a voltage to the first conductive support.

7. The method of claim 1, wherein forming a first detector complex comprises:
   contacting the first conductive substrate to a foreign conductive structure to cause the reduction of the first detector nanoparticle onto the first target nanoparticle.

8. The method of claim 1, wherein a first marker molecule is attached to the first target biomolecule.

9. The method of claim 1, wherein a first marker molecule is attached to the first target nanoparticle.

* * * * *